(12) United States Patent
Lilik et al.

(10) Patent No.: US 10,365,239 B2
(45) Date of Patent: Jul. 30, 2019

(54) METHOD AND SYSTEM FOR IN-SITU IDENTIFICATION OF WORKING FLUIDS

(71) Applicant: ExxonMobil Research and Engineering Company, Annandale, NJ (US)

(72) Inventors: Gregory K. Lilik, Media, PA (US); Spencer T. Stober, Bethlehem, PA (US); Alan M. Schilowitz, Highland Park, NJ (US); Michael L. Blumenfeld, Haddonfield, NJ (US); Gary James Johnston, Philadelphia, PA (US); Samuel C. Bainbridge, Houston, TX (US); Erik Herz, Conroe, TX (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 31 days.

(21) Appl. No.: 15/412,091

(22) Filed: Jan. 23, 2017

(65) Prior Publication Data
US 2017/0234819 A1 Aug. 17, 2017

Related U.S. Application Data

(60) Provisional application No. 62/295,269, filed on Feb. 15, 2016.

(51) Int. Cl.
*G06F 11/30* (2006.01)
*G01N 27/02* (2006.01)
(Continued)

(52) U.S. Cl.
CPC ........... *G01N 27/026* (2013.01); *G01N 21/25* (2013.01); *G01N 21/64* (2013.01); *G01N 21/643* (2013.01);
(Continued)

(58) Field of Classification Search
CPC .................................................. G01N 27/026
See application file for complete search history.

(56) References Cited

U.S. PATENT DOCUMENTS 6,274,381 B1  8/2001  Pauls et al.
6,779,505 B2  8/2004  Reischman et al.
(Continued)

FOREIGN PATENT DOCUMENTS

WO       200431332 A2     4/2004
WO   WO 2004031332 A2 *  4/2004   .......... C10M 171/00

OTHER PUBLICATIONS

International Search Report and Written Opinion PCT/US2017/014495 dated Apr. 7, 2017.
(Continued)

*Primary Examiner* — Phuong Huynh
(74) *Attorney, Agent, or Firm* — Anthony G. Boone (57) ABSTRACT

A system for in-situ identification of a working fluid disposed in at least one piece of equipment, the system including: a working fluid reservoir that contains the working fluid; an in-situ sensor disposed in the working fluid reservoir such that it detects properties of the working fluid or computes properties from the generated spectra of the working fluid; a transmitter that transmits the detected spectra of the working fluid and equipment identification information; and a cloud computing system that receives the detected spectra and the equipment identification information transmitted from the transmitter, wherein the cloud computing system compares the spectra and equipment identification information against a reference database to determine whether or not the spectra of the working fluid substantially matches the stored reference spectra associated with the expected or specified fluid for the equipment.

22 Claims, 6 Drawing Sheets

(51) Int. Cl.
*G01N 21/84* (2006.01)
*G01N 33/543* (2006.01)
*G01N 21/25* (2006.01)
*G01N 21/64* (2006.01)
*G01N 33/28* (2006.01)

(52) U.S. Cl.
CPC .............. *G01N 21/84* (2013.01); *G01N 27/02* (2013.01); *G01N 33/2882* (2013.01); *G01N 33/54373* (2013.01)

(56) References Cited

U.S. PATENT DOCUMENTS

| | | | |
|---|---|---|---|
| 7,157,611 | B2 | 1/2007 | Banavali et al. |
| 7,172,903 | B2 | 2/2007 | Schilowitz et al. |
| 7,241,621 | B2 | 7/2007 | Reischman et al. |
| 7,407,809 | B2 | 8/2008 | Reischman et al. |
| 7,442,936 | B2 | 10/2008 | Reischman et al. |
| 7,689,370 | B2 | 3/2010 | Grosser et al. |
| 7,741,122 | B2 | 6/2010 | Reischman |
| 7,915,048 | B2 | 3/2011 | Baxter et al. |
| 8,906,698 | B2 | 12/2014 | Croud et al. |
| 2004/0085080 | A1 | 5/2004 | Schilowitz et al. |
| 2004/0248307 | A1 | 12/2004 | Grof et al. |
| 2005/0035755 | A1 | 2/2005 | Schilowitz et al. |
| 2005/0110503 | A1 | 5/2005 | Koehler et al. |
| 2005/0184734 | A1 | 8/2005 | Sosnowski et al. |
| 2006/0118741 | A1 | 6/2006 | Ross et al. |
| 2013/0182241 | A1 | 7/2013 | Lawandy et al. |
| 2016/0242448 | A1 | 8/2016 | Ludscher et al. |

OTHER PUBLICATIONS

International Search Report and Written Opinion PCT/US2017/014493 dated Apr. 7, 2017.

\* cited by examiner

METHOD AND SYSTEM FOR IN-SITU IDENTIFICATION OF WORKING FLUIDS

CROSS-REFERENCE TO RELATED APPLICATIONS

This application claims the benefit of U.S. Provisional Application No. 62/295,269, filed on Feb. 15, 2016, the entire contents of which are incorporated herein by reference.

FIELD

A method and system for in-situ identification of a working fluid in a piece of equipment by inserting spectrum sensors, e.g., impedance/dielectric and/or visible/near infrared or infrared spectrum sensors, to detect the physical properties of the working fluid to generate a spectra of the working fluid which can be compared to a reference database to determine if the working fluid used meets the manufacture's original specifications, thereby avoiding warranty claims due to catastrophic equipment failure.

BACKGROUND

Working fluids, such as lubricating oils and hydraulic fluids, are important components of a wide variety of mechanical systems in which they provide one or more functions such as lubricating moving parts, transferring force or energy on the mechanical system, protecting parts against wear or even a combination of these. These fluids typically consist of hydrocarbon base oil formulated with numerous performance additives selected to enhance one or more performance characteristics of the working fluid.

Current practices for analyzing working fluid products rely on the manual removal of fluid samples from the reservoir for testing in a laboratory and typically pertain to the sensing of product condition, e.g., water content, soot content, property changes, etc. and are certainly not undertaken in real time. The process of sample extraction and shipment have a long lead-time for subsequent analysis and reporting. Such a lead-time could result in equipment damage if the equipment is operated with an improper or inadequately formulated fluid. Simple methods are also required to enable field measurements.

In many industrial environments regular fluid analysis by conventional laboratory methods is a standard modus operandi. This necessitates obtaining a sample of the fluid and transporting it, typically off-site, for analysis. This procedure normally takes at least three full days before the requisite analysis is completed and a report can be obtained. Such a time lag is highly undesirable. Many proposed methods for the on-line evaluation of the quality of lubricants are based on electrical measurements, such as the dielectric constant or impedance of the working fluid, with the measurements being taken at one fixed frequency or a multiplicity of frequencies. Since the best frequency for optimum sensitivity often depends on the properties or operational conditions of the working fluid it is preferred to make impedance measurements at a multiplicity of frequencies. One subset of impedance measurements is dielectric measurements.

Data obtained from time dependent impedance measurements are generally extremely complicated or convoluted. Additive degradation, base oil oxidation, temperature change, water and other polar species contamination, and viscosity changes of the lubricant oil can impact impedance properties of a lubricant oil. Solutions to this problem have been sought, and one such solution can be found in US Patent Publication No. 2005/0035755 (Schilowitz et al.), which is incorporated herein in its entirety by reference thereto.

Moreover, such analysis does not include the ability to verify if the working product sensed is proper for the article of equipment to which it is being used. There is also no such systems to provide anti-counterfeiting alerts or additive quantification alerts to the user.

The present disclosure does not require sample preparation, transport to an on-site or off-site laboratory and can be built into single purpose field instruments, as discuss hereafter.

It is an object of the present disclosure to provide a positive identification of fluid products. This will indicate if improper working fluids have been added to a working fluid reservoir. This will detect human error or product mislabeling and prevent it from causing potential harm to equipment.

Additionally, it is an object of the present disclosure to provide an alert to a user that indicates if counterfeit products have been introduced into the working fluid reservoir.

Furthermore, it is also an object to alert users when finished products have been properly additized.

Still, it is an object to alert users when the working fluid or equipment behavior is not normal versus previous behavior and average fleet behavior.

Yet another object is for the method and system of the present disclosure to alert and/or indicate if the hardware's operation is atypical compared to the average fleet behavior stored in the reference database.

Finally, it is an object of the present disclosure to provide, in addition to product verification, product condition sensing on a real time basis, e.g., water content, soot content, property changes, etc. to assist in product quality monitoring.

The present disclosure also provides many additional advantages, which shall become apparent as described below.

SUMMARY

A system for in-situ identification of a working fluid disposed in at least one piece of equipment, the system comprising: a working fluid reservoir that contains the working fluid; an in-situ sensor disposed in the working fluid reservoir such that it detects properties of the working fluid or computes properties from the generated spectra of the working fluid; a transmitter that transmits the detected spectra of the working fluid and equipment identification information; and a cloud computing system that receives the detected spectra and the equipment identification information transmitted from the transmitter, wherein the cloud computing system compares the spectra and equipment identification information against a reference database to determine whether or not the spectra of the working fluid substantially matches the stored reference spectra associated with the expected or specified fluid for the equipment.

The working fluid is at least one selected from the group consisting of: lubricants, hydraulic fluids, fuel and oil field chemicals.

The system further comprises a chemical marker added to the working fluid to assist in further identification of the working fluid. The chemical marker is at least one selected from the group consisting of: polyaromatic hydrocarbons, asphaltenes, detergents, ionic liquids, metallic nanoparticles, semi-conductor nanoparticles, fluorescent compounds, enzymes, DNA, RNA, polypeptides, fat soluble molecules with specific biological activity, redox-active organometallic complexes and arrays of molecules with unique molecular weight distributions.

The in-situ sensor is at least one sensor selected from the group consisting of: an impedance sensor, a dielectric sensor (using an AC or DC dielectric constant measurement), a visible/near infrared sensor, infrared sensor and sensors which utilize temperature to compensate for drift in the primary measured quantity. Preferably, it is helpful to use at least two in-situ sensors to increase the fidelity of the spectrum signals, wherein the multiple spectrum signals are combined, thereby generating a single multi-dimensional spectrum vector.

The system further comprises a data repository for storing the detected spectra and the equipment identification information.

The system also comprises a user interface for displaying the resulting output from the cloud computing system regarding whether or not the working fluid substantially matches the stored reference spectra associated with the equipment.

A method for in-situ identification of a working fluid disposed in a piece of equipment, the method comprising: detecting the properties of the working fluid via an in-situ sensor disposed in a working fluid reservoir; generating a spectra of the working fluid from the detected properties; transmitting the detected spectra of the working fluid and equipment identification information to a cloud computing system; and comparing the spectra and equipment identification information against a reference database to determine whether or not the working fluid substantially matches the stored reference spectra associated with the fluid, which is specified for a given lubrication system.

The method further comprises storing the detected spectra remotely on a cloud system, together with the equipment identification information.

The method also further comprises displaying the resulting output from the cloud computing system regarding whether or not the working fluid substantially matches the stored reference spectra associated with the equipment.

The method further comprises the steps of: (a) storing the spectra and equipment identification information of the working fluid if it does not match any working fluid spectra previously stored in the reference database; and (b) reporting a negative identification of the working fluid to a user.

The method further comprises reporting a negative identification of the working fluid to a user, if the spectra and equipment identification information of the working fluid does not match any working fluid spectra previously stored in the reference database.

The method further comprises reporting a positive identification of the working fluid to a user, if the spectra and equipment identification information of the working fluid matches a working fluid spectra previously stored in the reference database.

The method also includes an advanced algorithm or machine learning device, wherein the reference database is constantly updated to reflect real world effects on the detected spectra of the working fluid versus the initial reference spectra.

Further objects, features and advantages of the present disclosure will be understood by reference to the following drawings and detailed description.

DETAILED DESCRIPTION

All numerical values within the detailed description and the claims herein are modified by "about" or "approximately" the indicated value, and take into account experimental error and variations that would be expected by a person having ordinary skill in the art.

A method for the identification of working fluids, such as lubricating oils and hydraulic fluids, for the purposes of product verification, anti-counterfeiting, and additization quantification with an spectrum detector (sensor). A spectrum used for working fluid identification includes some combination of electric (impedance/dielectric) and/or visible/near infrared or infrared spectrum. The term "spectrum" can also refer to discrete measurements made at discrete frequencies and combined into a signal.

Furthermore, a chemical marker could be introduced to the working fluid to enhance the identification of the working fluid. Preferred chemical markers are selected from the group consisting of: polyaromatic hydrocarbons, asphaltenes, detergents, ionic liquids, oil-soluble ionic liquids (such as Trihexyl(tetradecyl)phosphonium bis(2,4,4-trimethylpentyl)phosphinate (THP-TMPP) and Tributyl(tetradecyl)phosphonium dodecylbenzenesulfonate (TBP-DDBS)), metallic nanoparticles and redox-active organometallic complexes. In various embodiments, the chemical marker is present in an amount greater than or equal to 0.1 wt %, or 0.2 wt %, or 0.3 wt %, based upon total weight of the working fluid. However, it will be understood that lower concentrations of chemical markers may be used, depending on sensitivity of the sensors utilized for detection.

A database of identified working fluids will be used as a reference for positive identification. An analogous database would be a Deoxyribonucleic acid (DNA) database used by geneticists to fined close or exact genetic matches.

The method also contains the transmission of raw or lightly processed sensor/detector data to a remote "cloud" where the raw signal will be processed and interpreted. The raw signal or the lightly processed signal is compared against a product reference database for positive identification of fluids, as well as providing an advanced algorithm or machine-learned comparison of the signal to what is normal behavior over time (i.e. synthesized from a series of sensors/detectors all transmitting data to the "cloud") for the operation of the lubricant in question via data analytics. The process or interpreted signal would then be transmitted from the cloud to a display interface or other data repository.

A method for ensuring product quality where a material, product or additive package is identified by a particular spectrum or signal or combination of spectra or signals and compared to a reference material, product or additive package. This embodiment could be relevant to lubricants, fuel, and oil field chemicals used in the upstream.

Finger print algorithms (similar to that of acoustics) can be used to identify sample spectra within a database. Spectra can be converted to sound and compared to the reference "song" or symphony. Anomaly detection learning algorithms (more robust than finger printing algorithms) can learn what is normal without any preceding information. These algorithms are data agnostic. The thresholds are dynamic and the algorithm is adaptive. In this way, when "normal" changes, this is alerted upon and the algorithm and the algorithm will adapt to the new normal when the fluid reservoir is not ideal or perhaps, predictive maintenance can occur to correct "normal" moving toward more ideal conditions.

Dielectric sensors can be, for example, selected from the group consisting of: coaxial-like, concentric-like ring, thin-film-like and plate-like probes. Such dielectric sensors can be either a conventional sensor or a smart sensor, i.e. conventional sensors only provide voltage for bulk processing since computer processing will be conducted in the cloud-based server, and smart sensors perform in-line processing, such as computing pressure based upon temperature compensation.

According to 2015 Top Technologies in Sensors & Control (D675-TI) by Frost & Sullivan "A smart sensor is, essentially, a sensor that possesses capabilities beyond merely detecting a certain parameter and sending a raw uncompensated signal. It includes electronics that condition the signal before the signal is transmitted to a control network or to its destination. Smart sensor functionality can include signal amplification, temperature compensation, analog-to-digital conversion, self-diagnostics, bus communications, and so on."

Sensors with smart capabilities can streamline the integration of sensors in an original equipment manufacturer (OEM)'s product or system. A smart sensor with the appropriate bus or network communications capability can be more easily implemented in a sensor network compared to a raw sensor. Smart Sensors are replacing conventional sensors in all the industries to enable lower cost and reduced complexity for OEMs. Smart sensors will play an enabling role in the Internet of Things revolution as more devices can be easily connected with each other.

Examples of preferred visible/near infrared or infrared spectrum sensors are as follows: Fourier transform infrared spectroscopy (FTIR), acousto-optical tunable filter (AOTF), bandpass filters Fourier transform infrared spectroscopy (FTIR), acousto-optical tunable filter (AOTF), band-pass filters.

It is possible to use both impedance/dielectric sensors and visible/near infrared or infrared spectrum sensors to provide a more positive identification of the working fluid. This results from the possibility that the unique measurements of each sensor may "see" attributes of the working fluid that are not visible to both sensors. By subsequently combining these unique (orthogonal) measurements, a larger amount of significant data is gathered for comparison the "composite reference spectrum database".

Figure 1:
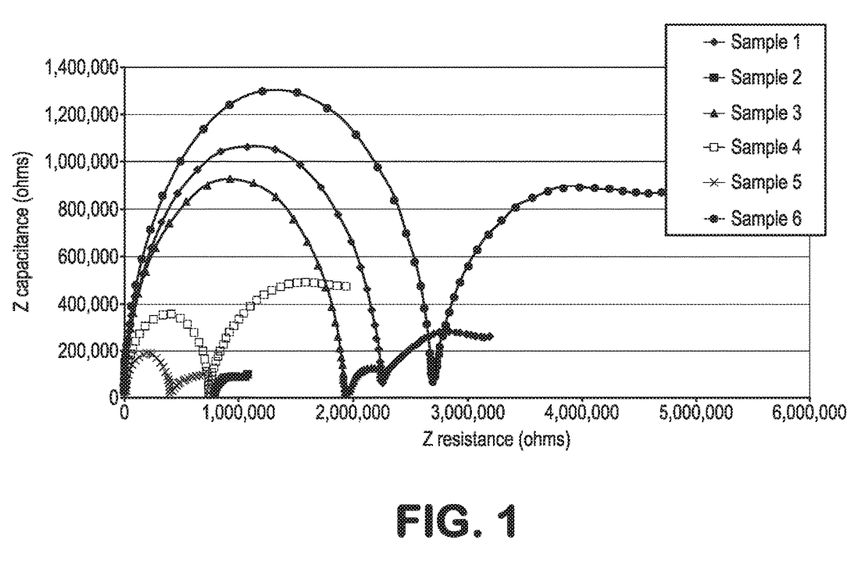
FIG. 1 is a chart which depicts the impedance spectrum measured for six fresh lubricant samples.

FIG. 1 shows the impedance spectrum measured for six fresh lubricant samples. The frequency response is plotted in a Nyquist plot, with Z-imaginary (capacitance) and Z-real (resistance) on the respective axis. In this case, the spectrometer was used to measure these quantities over the frequency range from 0.0075 Hz to 75 kHz. The lubricant samples which have unique formulations and additive packages produce an identifying spectral response to frequency. The unique measurement spectrum of a lubricant (or other working fluid) can be measured and added to a referenced database. The unique spectrum in the database can be used to provide positive identification of the lubricant, which has a reference spectrum. Other combinations of spectral measurements (infrared, Fourier transform infrared, and dielectric) can likewise be used to create a reference database of known working fluids to be used for positive identification.

The lubricant or other fluid can then be identified by computing the absolute difference in Zreal and Zimaginary between the spectrum of the unknown sample and each of the samples in the reference database, at each measured frequency. The reference spectrum that minimizes this difference, within a given tolerance, corresponds to the identity of the unknown sample.

Figure 2:
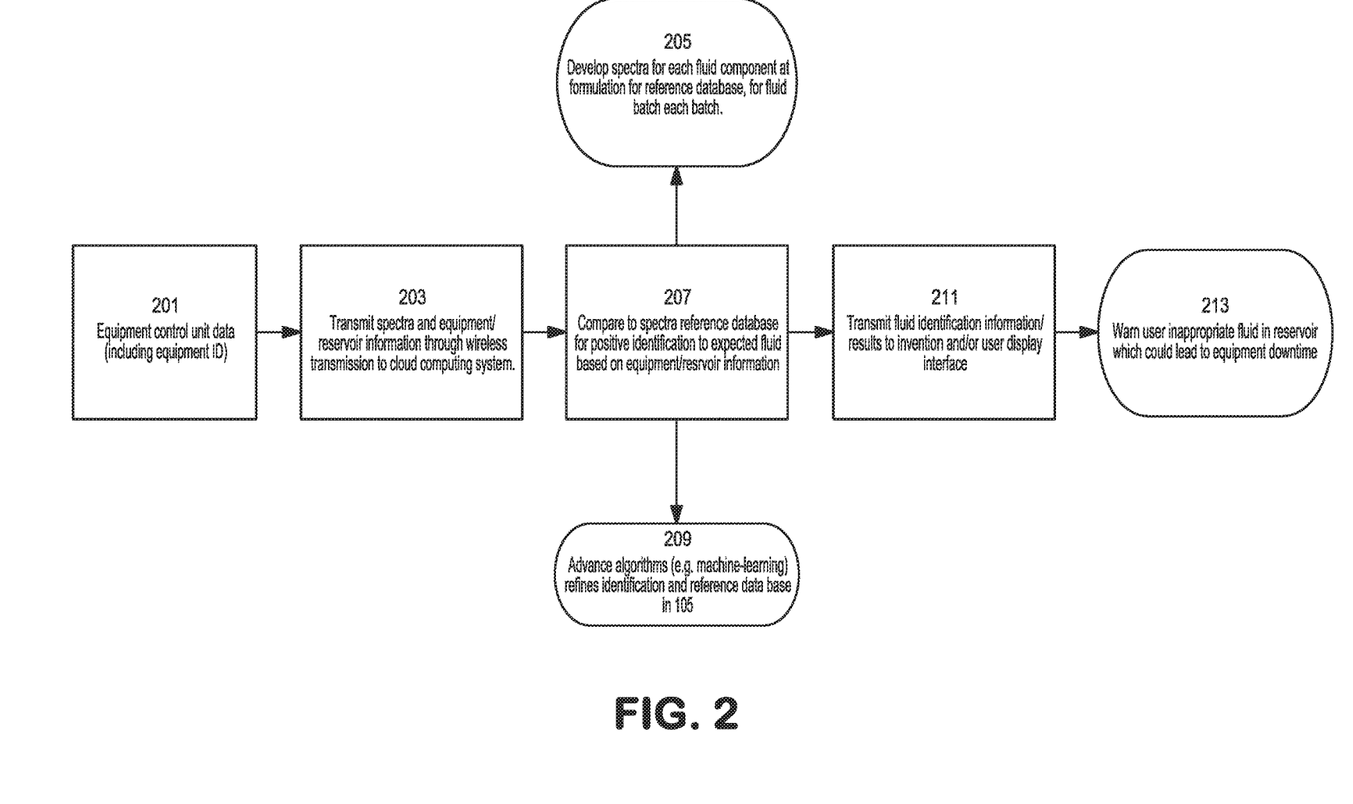
FIG. 2 is a flow chart of the system and method for determining if the proper working fluid has been added to a fluid reservoir according to the present disclosure.

The flow chart of FIG. 2 describes in detail the operation according to the present disclosure that determines if the proper fluid was added to a fluid reservoir.

An in-situ spectra and/or multiple spectrum (spectrum electric impedance/dielectric and visible/near infrared or infrared spectrum to further increase the fidelity) are measured for a new fluid added to a reservoir.

A novel aspect of the disclosure is the transmission of the unprocessed spectra or spectrums over wireless communications to a cloud computing system. A continuously updated database system is used for reference. Along with the spectra(s), the disclosure also transmits equipment/reservoir information, which indicates which batch of fluid is appropriate for the reservoir.

A continuously updated database system is used for reference and positive identification in the cloud system. Based on the transmitted equipment/reservoir information, a spectra of the undefined fluid is compared to the database of known fluid spectra.

A novel aspect of the current disclosure is the detailed reference spectra, which is specific to each fluid batch. Spectra are measured for fluid batch components incrementally during formulation. The spectra of the final formulation and incremental components are combined and processed as a reference, to be later used for positive identification. Another novel aspect of this disclosure is the combination and usage of multiple spectrum (electric (impedance/dielectric) and visible/near infrared or infrared spectrum) to further increase the fidelity of a fluid batch reference for later comparisons for positive identification.

The reference spectra database is continuously improved using an advanced algorithm (e.g. machine-learning algorithm) to refine the reference spectra to be a more accurate reference against a spectra measured in the field in a fluid reservoir under none ideal conditions. Another novel aspect is that the disclosure will periodically confirm that the fluid is normal and or expected compared to the reference database.

The identification of the fluid (based on the database) and an indication whether the appropriate fluid has been added to the reservoir is transmitted to the disclosure, user display interface and/or separate database repository.

If necessary a warning is supplied to the user via the display interface. This warning indicates if an appropriate fluid is in the reservoir and equipment, which could lead to equipment downtime. Furthermore, the disclosure provides an indication of a normal fluid or a warning of an unexpected fluid.

Figure 3:
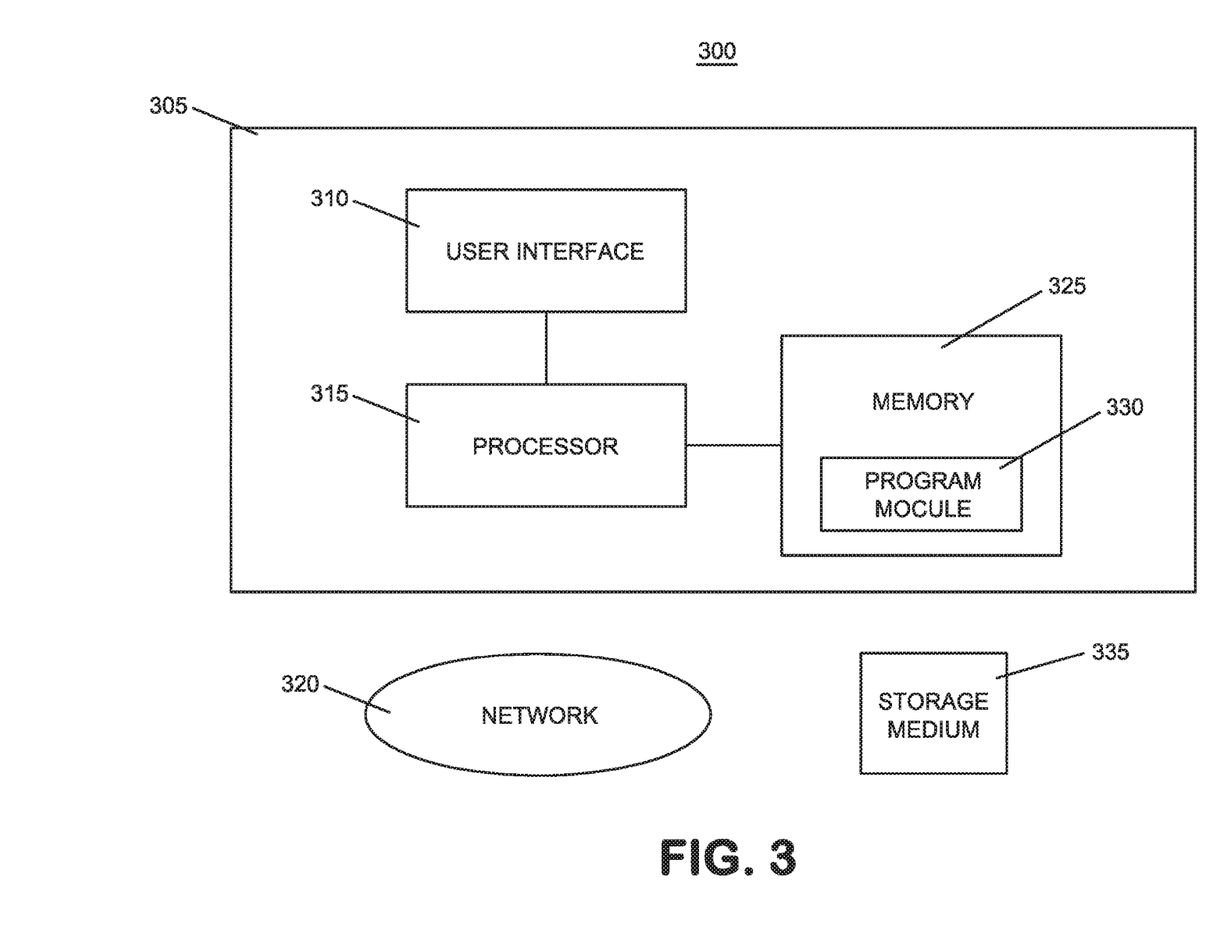
FIG. 3 is a block diagram of the computer system used according to the present disclosure.

FIG. 3 is a block diagram of a system 300, for employment of the present disclosure. System 300 includes a computer 305 coupled to a network 325, e.g., the Internet.

Computer 305 includes a user interface 310, a processor 315, and a memory 325. Computer 305 may be implemented on a general-purpose microcomputer. Although computer 305 is represented herein as a standalone device, it is not limited to such, but instead can be coupled to other devices (not shown) via network 320.

Processor 315 is configured of logic circuitry that responds to and executes instructions.

Memory 325 stores data and instructions for controlling the operation of processor 315. Memory 325 may be implemented in a random access memory (RAM), a hard drive, a read only memory (ROM), or a combination thereof. One of the components of memory 325 is a program module 330.

Figure 4:
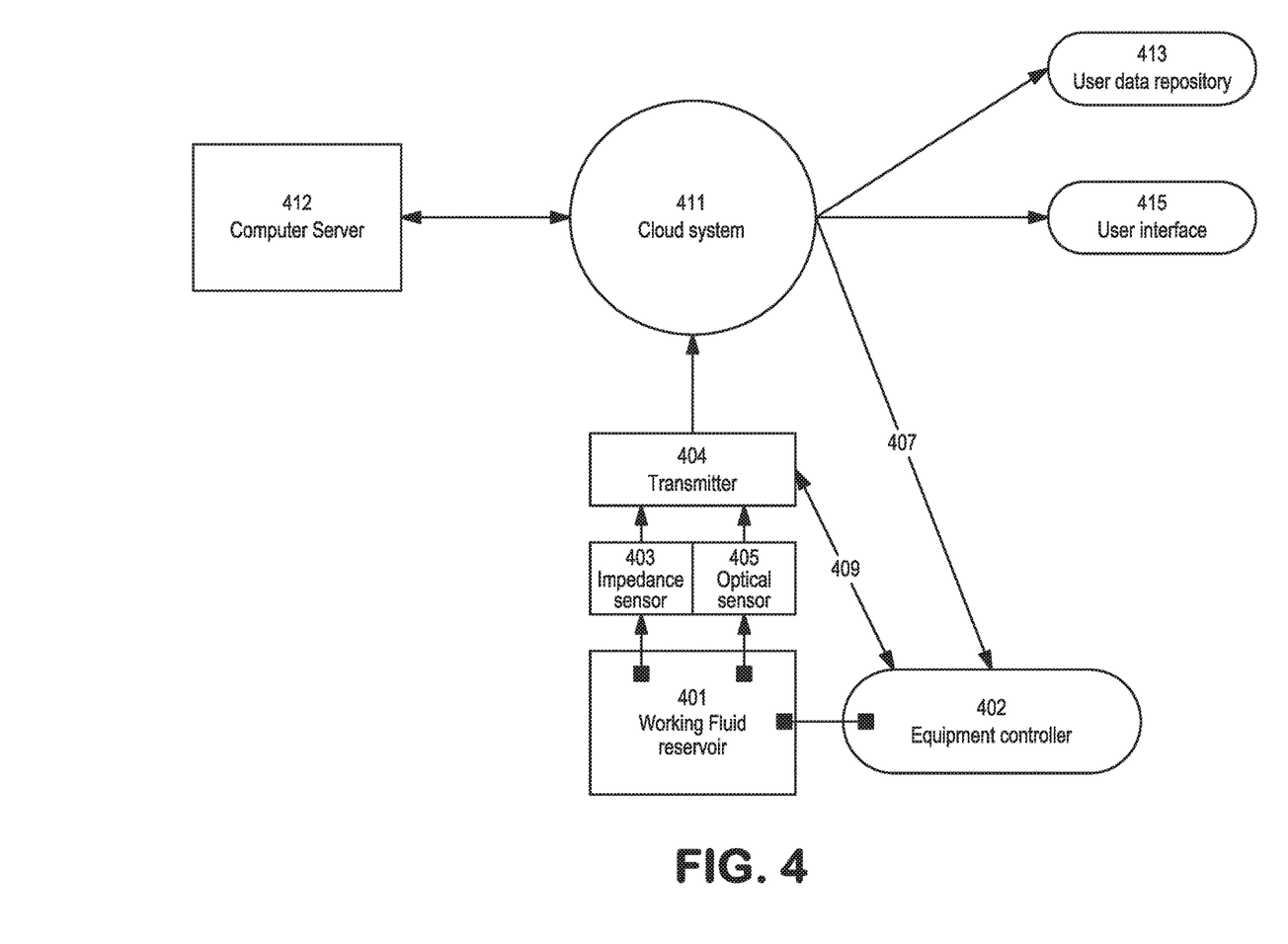
FIG. 4 is a block diagram of the in-situ product identification system according to the present disclosure.
Figure 5:
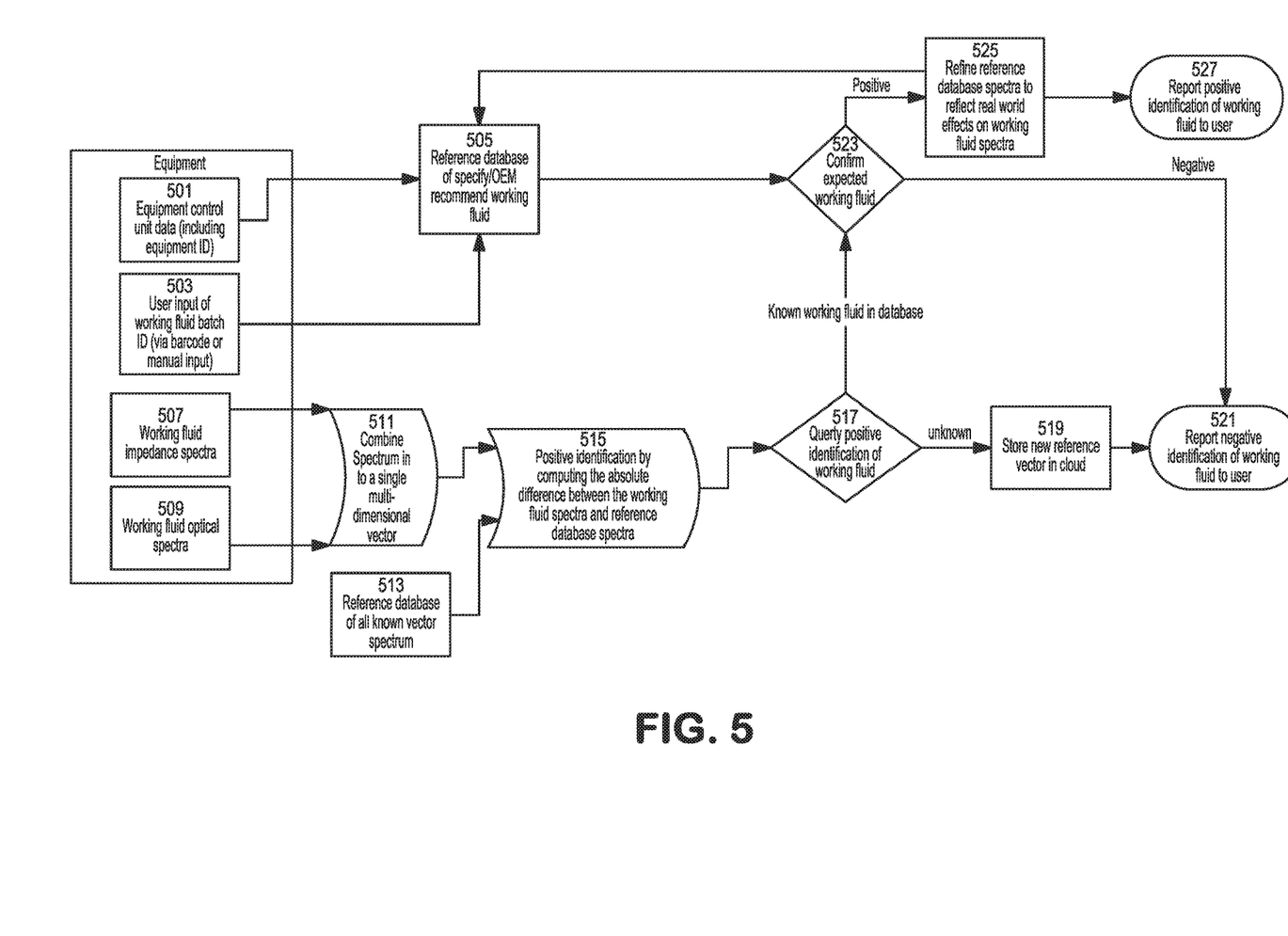
FIG. 5 is a logic diagram of working fluid identification method of the present disclosure.

Program module 330 contains instructions for controlling processor 315 to execute the methods described herein. For example, as a result of execution of program module 330, processor 315 execute the following steps: detecting the properties of the working fluid via an in-situ sensor (403, 405) disposed in a working fluid reservoir 401; generating a spectra of the working fluid (507, 509) from the detected properties; transmitting the detected spectra of the working fluid (507, 509) and equipment identification information 501 to a cloud computing system 411; and comparing the spectra (507, 509) and equipment identification information 501 against a reference database 505 to determine whether or not the working fluid substantially matches the stored reference spectra associated with the equipment (not shown). The term "module" is used herein to denote a functional operation that may be embodied either as a standalone component or as an integrated configuration of a plurality of sub-ordinate components. Thus, program module 330 may be implemented as a single module or as a plurality of modules that operate in cooperation with one another. Moreover, although program module 330 is described herein as being installed in memory 325, and therefore being implemented in software, it could be implemented in any of hardware (e.g., electronic circuitry), firmware, software, or a combination thereof.

User interface 310 includes an input device, such as a keyboard or speech recognition subsystem, for enabling a user to communicate information and command selections to processor 315. User interface 310 also includes an output device such as a display or a printer. A cursor control such as a mouse, track-ball, or joy stick, allows the user to manipulate a cursor on the display for communicating additional information and command selections to processor 315.

Processor 315 outputs, to user interface 310, a result of an execution of the methods described herein. Alternatively, processor 315 could direct the output to a remote device (not shown) via network 320.

While program module 330 is indicated as already loaded into memory 325, it may be configured on a storage medium 335 for subsequent loading into memory 325. Storage medium 335 can be any conventional storage medium that stores program module 330 thereon in tangible form. Examples of storage medium 335 include a floppy disk, a compact disk, a magnetic tape, a read only memory, an optical storage media, universal serial bus (USB) flash drive, a digital versatile disc, or a zip drive. Alternatively, storage medium 335 can be a random access memory, or other type of electronic storage, located on a remote storage system and coupled to computer 305 via network 320.

FIG. 4 is a block diagram of the in-situ product identification system 400 according to the present disclosure, wherein the equipment working fluid reservoir 401 can contain fluids such as lubricating oils or hydraulic fluids. Working fluid reservoir 401 is part of the same equipment system which contains the electronic equipment controller 402. At least one sensor, such as an impedance sensor 403 and/or a spectral sensor 405 are placed in-situ with working fluid reservoir 401 to produce real-time measurements of the working fluid. The signal from sensors (403 and/or 405) is either raw or is lightly processed for initial interpretation and compression for transmission. This lightly processed sensor information can indicate major issues with the working fluid, thus provides feed-back via communication line 407 to equipment controller 402 to immediately shutdown the equipment 409. Advanced processing of the sensor data will otherwise occur once transmitted, along with relevant equipment controller data sent via equipment controller 402, communication line 409, and transmitter 404 to Cloud System 411. Cloud System 411 is the data storage repository and connection nexus.

Sensor spectra and equipment controller data (including proscribed, OEM recommended working fluid) is transmitted to computer server 412 for positive identification. The measured spectra is compared to the reference spectra for positive identification. The reference spectra is updated to adjust for variation in real world measurements. The results and interpretation of comparison processing are transmitted to the user data repository 413, an user interface 415 and or to equipment controller 402 in the instance that the analysis indicates that an inappropriate working fluid has been introduced into working fluid reservoir 401, whereby immediate action can be taken to prevent equipment failure.

FIG. 5 is a logic diagram demonstrating the process flow and analysis according to the present disclosure, wherein equipment controller transmits data 501, e.g., equipment identification specifications, model, manufacturer, etc., and user input 503 related to the working fluid batch identification (via barcode or manual input) to a reference database of OEM (original equipment manufacturer) recommended working fluid 505.

Working fluid impedance spectra 507 and optical spectra 509 which are received from transmitter 404 are combined into a single multi-dimensional vector 511 in either the cloud system 411 or computer server 412. Computer server 412 computes the absolute difference between the working fluid spectra from 511 and reference database of all know vector spectrum 513 to determine if a positive identification of the working fluid can be determined 515. The system then seeks to determine whether a positive identification of the working fluid can be obtained 517. If there is no match to the detected working fluid, then the system stores this new reference vector in the cloud for future use 519 and reports to the user that it was not able to identify the working fluid 521 contained in working fluid reservoir 401. If there is a match between the detected spectrum and the reference spectrum, then the system confirms that the expected working fluid 523 by comparing the actual detected working fluid identification from 517 with the reference database of OEM recommended working fluid 505 for the specific equipment (not shown).

If there is a match between the actual working fluid identification 517 and reference database of OEM recommended working fluid 505, then update reference database spectra 505 via 525 to reflect real world effects on the working fluid spectra and thereafter report a positive identification of the working fluid to the user 527. If there is not a match between the actual working fluid identification 517 and reference database of OEM recommended working fluid 505, then the system reports that negative identification of the working fluid has been detected 521.

Figure 6:
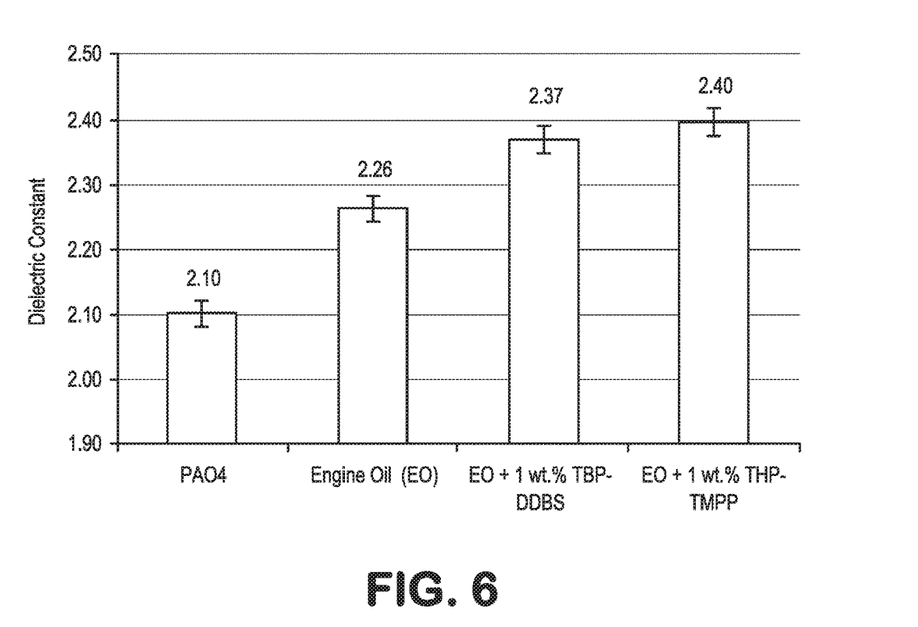
FIG. 6 illustrates the use of ionic liquids TBP-DDBS and THP-TMPP as chemical markers.

FIG. 6 illustrates use of ionic liquids TBP-DDBS and THP-TMPP to mark a finished engine oil lubricant such that it is identifiable by dielectric constant sensor at 80° C.

Figure 7:
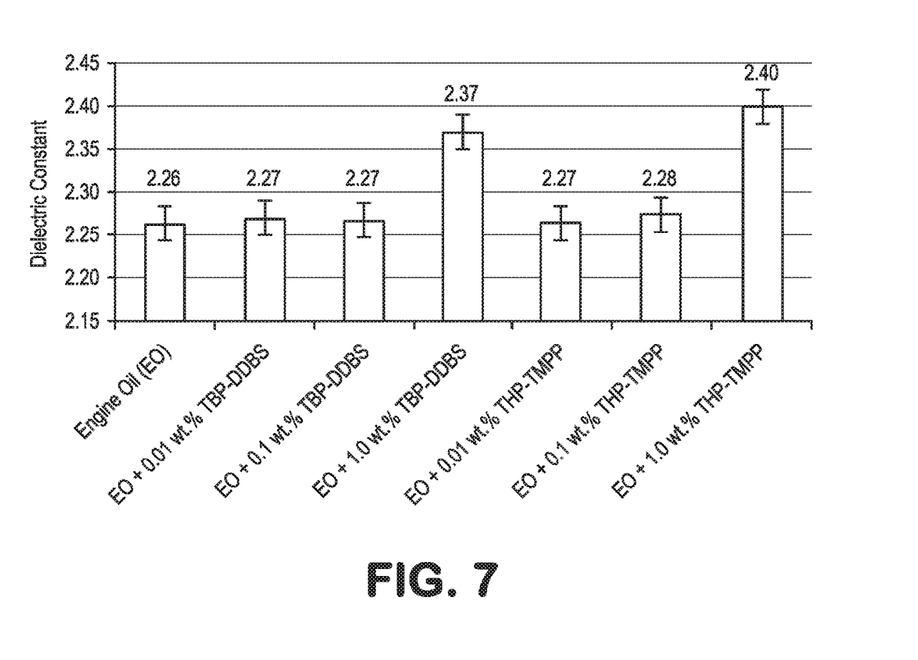
FIG. 7 illustrates the use of ionic liquids TBP-DDBS and THP-TMPP as chemical markers.

FIG. 7 illustrates the use of >0.1 wt. % of TBP-DDBS or THP-TMPP to mark finished lubricants for detection by a dielectric constant sensor at 80° C.

PCT and EP Clauses

1. A system (400) for in-situ identification of a working fluid disposed in a piece of equipment (402), said system comprising: a working fluid reservoir (401) that contains said working fluid; an in-situ sensor (403, 405) disposed in said working fluid reservoir (401) such that it detects the properties of said working fluid and generates a spectra of said working fluid; a transmitter (404) that transmits the detected spectra of said working fluid and equipment identification information; and a cloud computing system (411, 412) that receives said detected spectra and said equipment identification information transmitted from said transmitter (404), wherein said cloud computing system (411, 412) compares said spectra and equipment identification information against a reference database (505) to determine whether or not said working fluid substantially matches the stored reference spectra associated with said equipment (402).

2. The system (400) according to clause 1, wherein said working fluid is at least one selected from the group consisting of: lubricants, hydraulic fluids, fuel and oil field chemicals.

3. The system (400) according to clauses 1-2, further comprising a chemical marker added to said working fluid to assist in further identification of said working fluid, wherein said chemical marker is at least one selected from the group consisting of: polyaromatic hydrocarbons, asphaltenes, detergents, ionic liquids, oil-soluble ionic liquids (such as Trihexyl(tetradecyl)phosphonium bis(2,4,4-trimethylpentyl) phosphinate (THP-TMPP) and Tributyl(tetradecyl)phosphonium dodecylbenzenesulfonate (TBP-DDBS)), metallic nanoparticles, semi-conductor nanoparticles, fluorescent compounds, enzymes, DNA, RNA, polypeptides, fat soluble molecules with specific biological activity, redox-active organometallic complexes and arrays of molecules with unique molecular weight distribution.

4. The system (400) according to clauses 1-3, wherein said in-situ sensor (403, 405) is at least one sensor selected from the group consisting of: an impedance sensor, a dielectric sensor, a visible/near infrared sensor, and infrared sensor, preferably at least two in-situ sensors (403, 405) are used, and further comprising combining said detected spectra from said in-situ sensors, thereby generating a single multi-dimensional vector.

5. The system according to clauses 1-4, further comprising a data repository (413) for storing said detected spectra and said equipment identification information.

6. The system according to clauses 1-5, further comprising a user interface (415) for displaying the resulting output from said cloud computing system regarding whether or not said working fluid substantially matches said stored reference spectra associated with said equipment (402).

7. A method for in-situ identification of a working fluid disposed in a piece of equipment (402), said method comprising: detecting the properties of said working fluid via an in-situ sensor (403, 405) disposed in a working fluid reservoir (401); generating a spectra of said working fluid from said detected properties; transmitting the detected spectra of said working fluid and equipment identification information to a cloud computing system (411, 412); and comparing said spectra and equipment identification information against a reference database (5005) to determine whether or not said working fluid substantially matches the stored reference spectra associated with said equipment (402).

8. The method according to clause 7, further comprising storing said detected spectra and said equipment identification information.

9. The method according to clauses 7-8, further comprising displaying (415) the resulting output from said cloud computing system regarding whether or not said working fluid substantially matches said stored reference spectra associated with said equipment.

10. The method according to clauses 7-9, further comprising the steps of: (a) storing said spectra and equipment identification information of said working fluid if it does not match any working fluid spectra previously stored in said reference database; and (b) reporting a negative identification of said working fluid to a user.

11. The method according to clauses 7-10, further comprising reporting a negative identification of said working fluid to a user, if said spectra and equipment identification information of said working fluid does not match any working fluid spectra previously stored in said reference database, or reporting a positive identification of said working fluid to a user, if said spectra and equipment identification information of said working fluid matches a working fluid spectra previously stored in said reference database.

12. The method according to clauses 7-11, further comprising updating said reference database to reflect real world effects on the detected spectra of said working fluid.

While we have shown and described several embodiments in accordance with our invention, it is to be clearly understood that the same may be susceptible to numerous changes apparent to one skilled in the art. Therefore, we do not wish to be limited to the details shown and described but intend to show all changes and modifications that come within the scope of the appended claims.

The invention claimed is:

1. A system for in-situ identification of a working fluid disposed in at least one piece of equipment, said system comprising:
   a working fluid reservoir that contains said working fluid;
   an in-situ sensor disposed in said working fluid reservoir such that it detects properties of said working fluid or computes properties from the generated spectra of said working fluid;
   a transmitter that transmits a detected spectra of said working fluid and equipment identification information; and
   a cloud computing system that receives said detected spectra and said equipment identification information transmitted from said transmitter,
   wherein said cloud computing system compares said detected spectra and equipment identification information against a reference database to determine whether or not the detected spectra of the working fluid substantially matches the stored reference spectra associated with the expected or specified fluid for said equipment.

2. The system according to claim 1, wherein said working fluid is at least one selected from the group consisting of: lubricants, hydraulic fluids, fuel and oil field chemicals.

3. The system according to claim 1, wherein said in-situ sensor comprises at least two sensors selected from the group consisting of: an impedance sensor, a dielectric sensor, a visible/near infrared sensor, and infrared sensor wherein the spectrum signals from each sensor are combined.

4. The system according to claim 3, further comprising a chemical marker added to said working fluid to assist in further identification of said working fluid wherein said chemical marker is at least one selected from the group consisting of: polyaromatic hydrocarbons, asphaltenes, detergents, ionic liquids, metallic nanoparticles, semi-conductor nanoparticles, fluorescent compounds, enzymes, DNA, RNA, polypeptides, fat soluble molecules with specific biological activity, redox-active organometallic complexes and arrays of molecules with unique molecular weight distributions.

5. The system according to claim 1, wherein said in-situ sensor is at least one sensor selected from the group consisting of: an impedance sensor, a dielectric sensor, a visible/near infrared sensor, and infrared sensor.

6. The system according to claim 1, further comprising a data repository for storing said detected spectra and said equipment identification information.

7. The system according to claim 1, further comprising a user interface for displaying the resulting output from said cloud computing system regarding whether or not said working fluid substantially matches said stored reference spectra associated with said equipment.

8. A method for in-situ identification of a working fluid disposed in a piece of equipment, said method comprising:
   detecting the properties of said working fluid via an in-situ sensor disposed in a working fluid reservoir;
   generating a detected spectra of said working fluid from said detected properties;
   transmitting the detected spectra of said working fluid and equipment identification information to a cloud computing system; and
   comparing said spectra and equipment identification information against a reference database to determine whether or not said working fluid substantially matches the stored reference spectra associated with said equipment.

9. The method according to claim 8, wherein said working fluid is at least one selected from the group consisting of: lubricants, hydraulic fluids, fuel and oil field chemicals.

10. The method according to claim 8, wherein said in-situ sensor comprises at least two sensors selected from the group consisting of: an impedance sensor, a dielectric sensor, a visible/near infrared sensor, and infrared sensor wherein the spectrum signals from each sensor are combined.

11. The method according to claim 10, further comprising adding a chemical marker to said working fluid to assist in further identification of said working fluid wherein said chemical marker is at least one selected from the group consisting of: polyaromatic hydrocarbons, asphaltenes, detergents, ionic liquids, metallic nanoparticles, semi-conductor nanoparticles, fluorescent compounds, enzymes, DNA, RNA, polypeptides, fat soluble molecules with specific biological activity, redox-active organometallic complexes and arrays of molecules with unique molecular weight distributions.

12. The method of claim 10, wherein the chemical marker is an oil-soluble ionic liquid.

13. The method of claim 12, wherein the oil-soluble ionic liquid is selected from Trihexyl(tetradecyl)phosphonium bis (2,4,4-trimethylpentyl)phosphinate (THP-TMPP) and Tributyl(tetradecyl)phosphonium dodecylbenzenesulfonate (TBP-DDBS).

14. The method of claim 13, wherein the oil-soluble ionic liquid is present in a concentration greater than or equal to 0.1 wt %, based upon total weight of the working fluid.

15. The method according to claim 8, wherein said in-situ sensor is at least one sensor selected from the group consisting of: an impedance sensor, a dielectric sensor, a visible/near infrared sensor, and infrared sensor.

16. The method according to claim 15, wherein at least two in-situ sensors are used, and further comprising combining said detected spectra from said in-situ sensors, thereby generating a single multi-dimensional vector.

17. The method according to claim 8, further comprising storing said detected spectra and said equipment identification information.

18. The method according to claim 8, further comprising displaying the resulting output from said cloud computing system regarding whether or not said working fluid substantially matches said stored reference spectra associated with said equipment.

19. The method according to claim 8, further comprising the steps of: (a) storing said spectra and equipment identification information of said working fluid if it does not match any working fluid spectra previously stored in said reference database; and (b) reporting a negative identification of said working fluid to a user.

20. The method according to claim 8, further comprising reporting a negative identification of said working fluid to a user, if said spectra and equipment identification information of said working fluid does not match any working fluid spectra previously stored in said reference database.

21. The method according to claim 8, further comprising reporting a positive identification of said working fluid to a user, if said spectra and equipment identification information of said working fluid matches a working fluid spectra previously stored in said reference database.

22. The method according to claim 18, further comprising updating said reference database to reflect real world effects on the detected spectra of said working fluid.

* * * * *